US00PP29563P2

(12) United States Plant Patent
Hartman

(10) Patent No.: US PP29,563 P2
(45) Date of Patent: Jul. 31, 2018

(54) ***CALADIUM* PLANT NAMED 'DAY DREAMER'**

(50) Latin Name: *Caladium X hortulanum*
Varietal Denomination: Day Dreamer

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 15/530,469

(22) Filed: Jan. 18, 2017

(51) Int. Cl.
*A01H 5/12* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — C. A. Whealy

(57) ABSTRACT

A new and distinct cultivar of *Caladium* plant named 'Day Dreamer', characterized by its short to intermediate height and mounding plant habit; leaf petioles that are upright to outwardly leaning with development; vigorous growth habit and rapid growth rate; strap (or lance) type leaves that are medium green in color with greenish white-colored venation surrounded with white areas and interveinal areas that are white variably tinged with purplish pink in color with random dark red-colored flecks and spots; and petioles that are pink in color with dark green-colored streaks, stipples and tessellations.

4 Drawing Sheets

Botanical designation: *Caladium* X *hortulanum*.
Cultivar denomination: 'DAY DREAMER'.

BACKGROUND OF THE INVENTION

The present invention relates to a new and distinct cultivar of *Caladium* plant, botanically known as *Caladium* X *hortulanum*, commercially referred to as a strap (or lance) leaf-type *Caladium* and hereinafter referred to by the name 'Day Dreamer'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2008 in Avon Park, Fla. of *Caladium* X *hortulanum* 'Gingerland', not patented, as the female, or seed, parent with *Caladium* X *hortulanum* 'White Wonder', disclosed in U.S. Plant Pat. No. 21,044, as the male, or pollen, parent. The new *Caladium* plant was discovered and selected by the Inventor as a single plant within the progeny of the stated cross-pollination in a controlled outdoor nursery environment in Zolfo Springs, Fla. in September, 2009.

Asexual reproduction of the new *Caladium* plant by 'chipping' the tubers (cutting the tuber into segments with each segment containing an axillary bud and tuber cortical tissue) in a controlled outdoor nursery environment in Zolfo Springs, Fla. since April, 2010 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Day Dreamer'. These characteristics in combination distinguish 'Day Dreamer' as a new and distinct *Caladium* plant:

1. Short to intermediate in height and mounding plant habit; leaf petioles upright to outwardly leaning with development.
2. Vigorous growth habit and rapid growth rate.
3. Strap (or lance) type leaves that are medium green in color with greenish white-colored venation surrounded with white areas and interveinal areas that are white variably tinged with purplish pink in color with random dark red-colored flecks and spots.
4. Petioles that are pink in color with dark green-colored streaks, stipples and tessellations.

Plants of the new *Caladium* differ primarily from plants of the female parent, 'Gingerland', in the following characteristics:

1. Plants of the new *Caladium* are shorter, denser and more mounding than plants of 'Gingerland'.
2. Plants of the new *Caladium* grow faster than plants of 'Gingerland'.
3. Plants of the new *Caladium* and 'Gingerland' differ in leaf color as leaves of 'Gingerland' have white-colored interveinal areas, white and pink-colored venation, dark red-colored spots and dark green-colored borders.

Plants of the new *Caladium* differ primarily from plants of the male parent, 'White Wonder', in the following characteristics:

1. Plants of the new *Caladium* are taller than plants of 'White Wonder'.
2. Plants of the new *Caladium* and 'White Wonder' differ in leaf color as leaves of 'White Wonder' are white to grey-green in color with light pink to white-colored venation and dark green-colored borders.

Plants of the new *Caladium* can be compared to plants of *Caladium* X *hortulanum* 'White Dynasty', disclosed in U.S. Plant Pat. No. 22,240. In side-by-side comparisons, plants of the new *Caladium* differ primarily from plants of 'White Dynasty' in the following characteristics:

1. Plants of the new *Caladium* are shorter and more mounding than plants of 'White Dynasty'.
2. Plants of the new *Caladium* and 'White Dynasty' differ in leaf color as leaves of 'White Dynasty' are white and greyed green in color with few random red purple-colored spots, dark green-colored margins and greyed green-colored venation.

Plants of the new *Caladium* can be compared to plants of *Caladium* X *hortulanum* 'Mount Everest', disclosed in U.S. Plant Pat. No. 18,764. In side-by-side comparisons, plants of the new *Caladium* differ primarily from plants of 'Mount Everest' in the following characteristics:

1. Plants of the new *Caladium* are shorter, denser and more mounding than plants of 'Mount Everest'.
2. Plants of the new *Caladium* and 'Mount Everest' differ in leaf color as leaves of 'Mount Everest' are creamy white to grey green in color with dark green-colored margins and cream to pinkish red-colored venation.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Day Dreamer' in a container and grown in a shadehouse (tuber de-eyed).

The photograph at the top of the second sheet is a comparison view of typical potted plants of the female parent, 'Gingerland' (left), 'Day Dreamer' (center) and the male parent, 'White Wonder' (right).

The photograph at the bottom of the second sheet is a comparison view of typical potted plants of 'White Dynasty' (left), 'Day Dreamer' (center) and 'Mount Everest' (right).

The photograph at the top of the third sheet is a side perspective view of typical plants of 'Day Dreamer' grown in an open field.

The photograph at the bottom of the third sheet is a comparison view of typical plants of 'Day Dreamer' grown in containers; the plant on the left has not had its tuber de-eyed and the plant on the right has had its tuber de-eyed prior to planting.

The photograph at the top of the fourth sheet is a close-up view of a typical inflorescence of 'Day Dreamer'.

The photograph at the bottom of the fourth sheet is a close-up view of typical freshly-harvested tubers with roots and leaf petioles of 'Day Dreamer'.

DETAILED BOTANICAL DESCRIPTION

The aforementioned photographs and following observations and measurements describe plants grown in 15-cm containers in a polypropylene-covered shadehouse (50% light reduction) in Avon Park, Fla. and plants grown in ground beds under full sunlight conditions in an outdoor nursery in Crewsville, Fla. The plants were grown under cultural practices typical of commercial shadehouse and outdoor nursery production. During the production of the shadehouse-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from about 10,000 to 12,000 foot-candles. Plants grown in the shadehouse were eight weeks old and plants grown in the outdoor nursery were six months old when the photographs and the detailed description were taken. In the following description, color references are made to The Royal Horticultural Society Colour Chart, 2001 Edition, except where general terms of ordinary dictionary significance are used.

Botanical classification: *Caladium* X *hortulanum* 'Day Dreamer'.

Parentage:

*Female, or seed, parent.*—*Caladium* X *hortulanum* 'Gingerland', not patented.

*Male, or pollen, parent.*—*Caladium* X *hortulanum* 'White Wonder', disclosed in U.S. Plant Pat. No. 21,044.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented; individual segments irregularly elliptic to ovate in shape. Height: About 3.3 cm. Diameter: About 5.2 cm to 7.4 cm. Segment height: About 2 cm to 2.8 cm. Segment diameter: About 2 cm to 3.3 cm. Texture: Thick, starchy; somewhat brittle. Color: Epidermis, freshly-harvested: Close to N170D and 159B. Epidermis, dried: Close to 200A to 200B. Cortical tissue: Close to 11D and 4C. Axillary buds: Close to 36B and 36C. Root description: Thick, fleshy contractile roots with few lateral branches; color, close to N155D. Rooting habit: Dense.

Plant description:

*Plant type.*—Herbaceous perennial; suitable as a potted plant in containers 15-cm to 25-cm and suitable as a landscape plant in shaded areas.

*Plant and growth habit.*—Short to intermediate in height and mounding plant habit; vigorous growth habit and rapid growth rate; potted plants in finished or saleable form in about six weeks after planting tubers; leaf petioles and leaves arise from one or more growing points on tubers; petioles mostly upright and outwardly leaning with development; inflorescences held above the foliar plane on strong upright scapes.

*Plant height, from soil level to top of foliar plane, shadehouse-grown potted plants.*—About 27 cm to 31 cm.

*Plant height, from soil level to top of inflorescences, shadehouse-grown potted plants.*—About 35 cm.

*Plant diameter or spread, shadehouse-grown potted plants.*—About 36 cm to 44 cm.

*Number of shoots per plant, shadehouse-grown potted plants, tubers not de-eyed.*—About three to four develop per #1 tuber.

*Number of shoots per plant, shadehouse-grown potted plants, tubers de-eyed.*—About four to five develop per #1 tuber.

*Cataphylls, shadehouse-grown potted plants.*—Length: About 6 cm to 8 cm. Width: About 1.2 cm to 1.6 cm. Shape: Lanceolate to narrowly elliptic. Apex: Cuspidate. Base: Sheathing the stem. Color, inner surface: Close to N155B; colors and patterns on the outer surface are visible on the inner surface. Color, outer surface: Close to 36D and N170D; streaked and stippled with close to 200B tinged with close to 147A; with development, color becoming closer to 199A and 200A and stained with close to 187A.

Leaf description:

*Arrangement and type.*—Alternate; simple; strap (or lance)-type.

*Length, shadehouse-grown potted plants.*—About 14.5 cm to 19 cm.

*Width, shadehouse-grown potted plants.*—About 8.5 cm to 11 cm; when flattened, about 10 cm to 12 cm.

*Blade aspect.*—Angled upwardly along the midrib.

*Shape.*—Ovate.

*Apex.*—Acute.

*Base.*—Sagittate to peltate.

*Margin.*—Entire; wavy with broad undulations.

*Texture, upper and lower surfaces.*—Smooth, glabrous; rigid.

*Luster, upper surface.*—Dull sheen.

*Luster, lower surface.*—Glaucous, dull sheen.

*Venation pattern.*—Pinnate.

*Color, shadehouse-grown potted plants.*—Developing leaves, upper surface: Background color: Close to 147A. Margins: Close to 147A; at the edge, close to 187A. Basal notch: Close to 187A and 187B. Midvein: Close to 155C and 194D may be tinged with close to 184D. Primary venation: Close to 194B. Areas surrounding venation: Close to 155C and 193D. Interveinal areas: Close to 155C or close to 155C variably flushed with close to 184D; random sectors, close to 193D and 137B. Random spots: Close to 187A to 187B tinged with close to 53A. Developing leaves, lower surface: Background color: Close to 191A. Margins: Close to 191A; at the edge, close to 187A. Basal notch: Close to 187B. Midvein and primary venation: Close to 155B or close to 155B tinged with close to 194D. Areas surrounding venation: Close to 155C. Interveinal areas: Close to 147C, 147D, 155C or close to 155C variably flushed with close to 187D. Random spots: Close to 187A and 187B. Fully expanded leaves, upper surface: Background color: Close to 147A. Margins: Close to 147A; at the edge, close to 187A. Basal notch: Close to 187A. Midvein: Close to 155C or close to 155C variably tinged with close to 184C to 184D. Primary venation: Close to 194D. Areas surrounding venation: Close to 155C. Interveinal areas: Close to 155C or close to 155C variably flushed with close to 184C to 184D; random sectors, close to 193D and 137B. Random spots: Close to 187A tinged with close to 53A. Fully expanded leaves, lower surface: Background color: Close to 191A and 191B. Margins: Close to 191A and 191B; at the edge, close to 187A. Basal notch: Close to 187A. Midvein and primary venation: Close to 155B or close to 155B tinged with close to 194D. Areas surrounding venation: Close to 155C. Interveinal areas: Close to 147C, 155C or close to 155C variably flushed with close to 187C and 187D. Random spots: Close to 187A and 187B.

*Petioles.*—Aspect: Initially upright and straight; with development, somewhat outwardly leaning; flexible. Length, shadehouse-grown potted plants: About 20 cm to 23 cm. Diameter, distally, shadehouse-grown potted plants: About 3.5 mm to 5 mm. Diameter, proximally, shadehouse-grown potted plants: About 8 mm to 11 mm. Texture: Smooth, glabrous. Color, shadehouse-grown potted plants: Close to 182D and N170D streaked, stippled and tessellated with close to 147A tinged with close to 200B; below the leaf and petiole junction, close to N170D tinged with close to 182D. Wing length, shadehouse-grown potted plants: About 3.8 cm to 5.5 cm. Wing diameter, shadehouse-grown potted plants: About 8 mm to 10 mm. Texture and luster, inner and outer surfaces: Smooth, glabrous; dull to slightly glossy. Wing color, shadehouse-grown potted plants: Inner surface: Close to N155B; colors and patterns on the outer surface are visible on the inner surface. Outer surface: Close to 182D and N170D stippled, streaked and tessellated with close to 147A tinged with close to 200B.

Inflorescence description:

*Inflorescences observed on eight week-old shadehouse-grown potted plants.*

*Inflorescence arrangement.*—Upright hooded spathes surrounding a columnar spadix borne on a tall upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance.*—Night-fragrant; sweet, jasmine-like with camphor note.

*Natural flowering season and flower longevity.*—Plants of the new *Caladium* typically flower during the spring in central Florida; flowers develop about eight weeks after growth commences; inflorescences last about three days before fading; inflorescences persistent.

*Spathe.*—Length, overall: About 14 cm. Length, distal open portion: About 10 cm. Length, proximal closed portion: About 4 cm. Width, distal open portion: About 4.8 cm. Depth, distal open portion: About 2.3 cm. Width, at constriction: About 1.4 cm. Width, proximal closed portion: About 2.4 cm. Shape, open portion: Elliptic. Apex: Acute. Base: Obtuse. Margin: Entire. Texture, front and rear surfaces: Smooth, glabrous. Luster, front surface: Dull sheen. Luster, rear surface: Dull sheen; proximally, glaucous. Color, front surface: Distal open portion: Close to 155C with sparse speckles and spots, close to 53A tinged with close to 187B; distally, with development, color becoming closer to 199B. Proximal closed portion: Close to 194C; proximally sparsely streaked and tinged with close to 187A to 187B; color does not change with development. Color, rear surface: Distal open portion: Close to 155C and 145D; color does not change with development. Proximal closed portion: Close to 147A and 147B; color does not change with development.

*Spadix*.—Length, overall: About 7.5 cm. Length, male flower zone: About 4.8 cm. Length, sterile zone: About 1.4 cm. Length, female flower zone: About 1.4 cm. Diameter, male flower zone: About 1.1 cm. Diameter, sterile flower zone: About 1 cm. Diameter, female flower zone: About 1.1 cm. Shape: Columnar, spindle-shaped. Apex: Acute to obtuse. Base: Obtuse. Aspect: Upright. Color, mature, male zone: Close to 155C to 155D. Color, mature, sterile zone: Close to 155C to 155D. Color, mature, female zone: Close to 159C and N170D. Male flowers: Quantity per spadix: About 140. Shape: Obovate. Height: About 3 mm. Diameter: About 3 mm. Pollen amount: Moderate. Pollen color: Close to 4C. Female flowers: Quantity per spadix: About 135. Shape: Obovate. Height: About 3 mm. Diameter: About 2 mm. Stigma color: Close to 159C. Ovary color: Close to N170D.

*Scape*.—Length: About 21 cm. Diameter: About 7.5 mm. Strength: Sturdy; flexible. Aspect: Mostly erect. Texture and luster: Smooth, glabrous; dull sheen. Color: Close to 148A and 147A, streaked and stippled with close to 200B and 200C; distally, close to 147B and 147C, faintly stippled and streaked with close to 200D.

*Seeds and fruits*.—To date, seed and fruit development have not been observed on plants of the new *Caladium*.

Disease & pest tolerance: Plants of the new *Caladium* have been observed to have average tolerance to *Pythium* Root Rot and above average tolerance to *Xanthomonas* Leaf Spot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11. In cooler zones, tubers can be "lifted" prior to first freeze and stored in a cool dry environment overwinter for re-planting the following spring.

It is claimed:

1. A new and distinct *Caladium* plant named 'Day Dreamer' as illustrated and described.

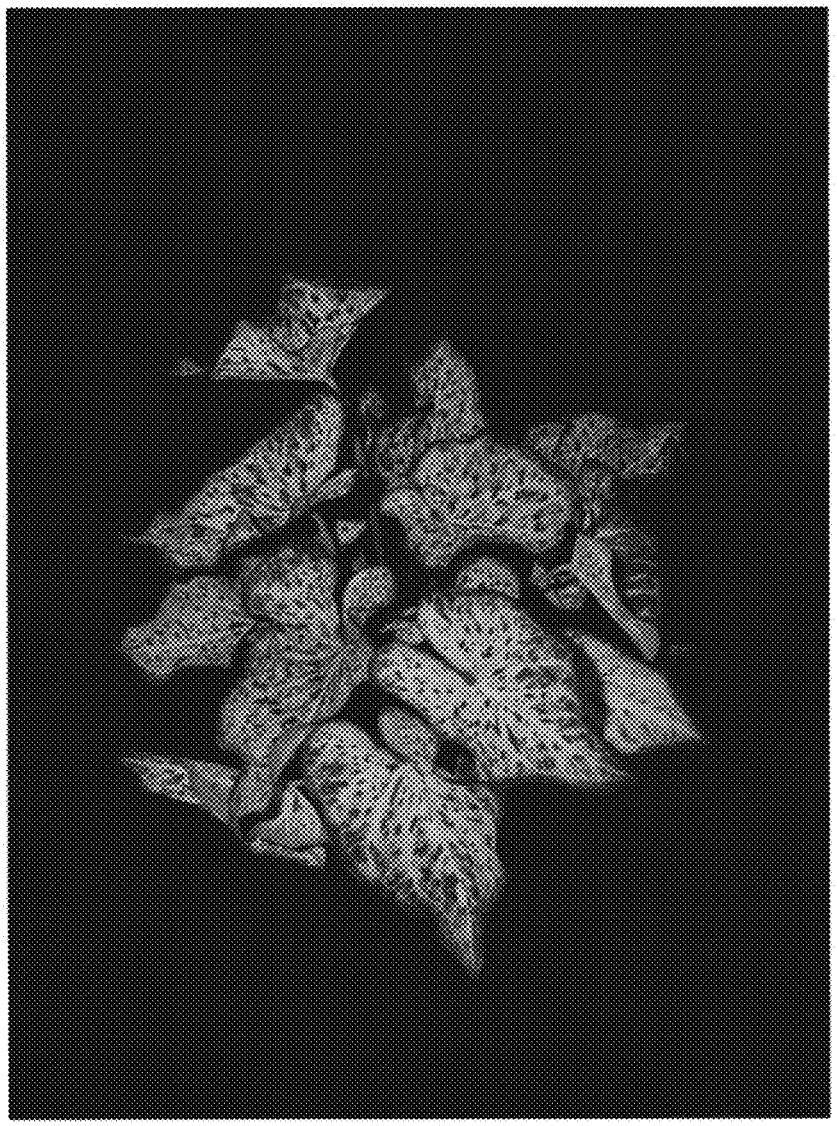

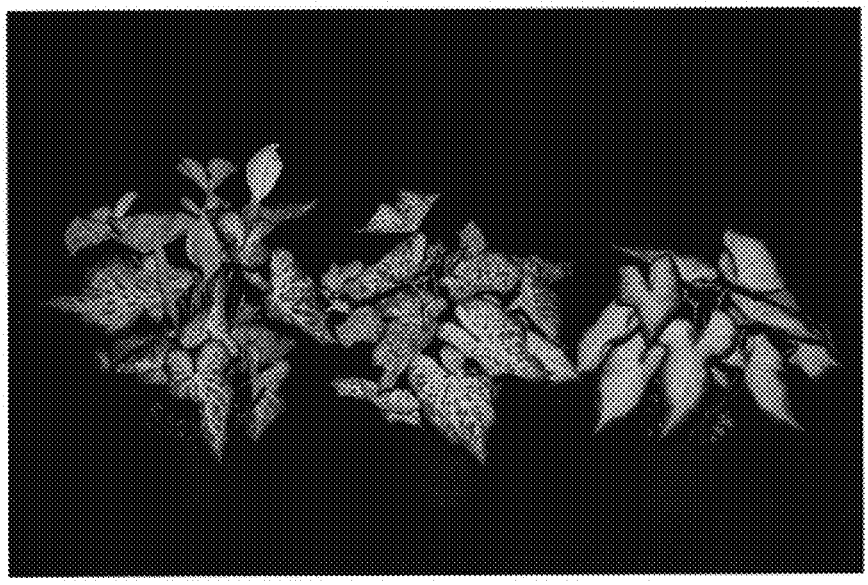
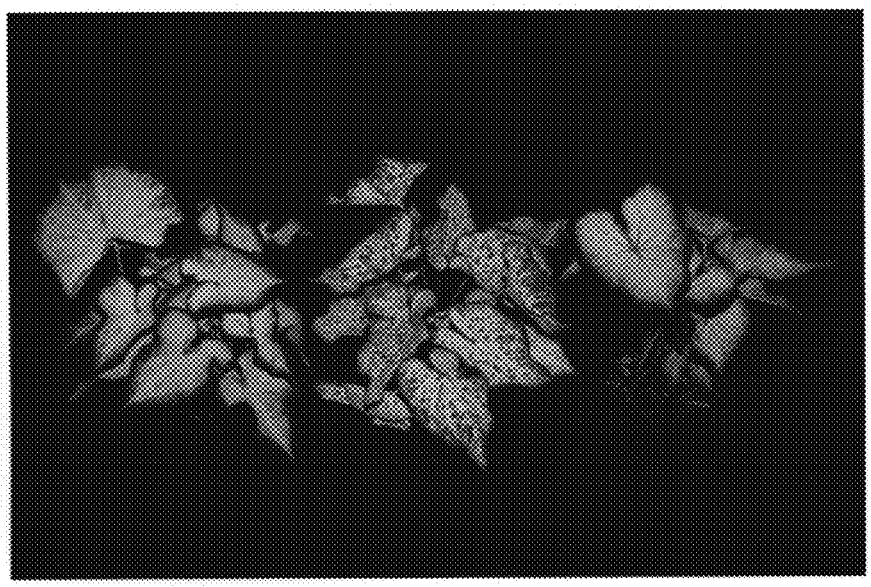

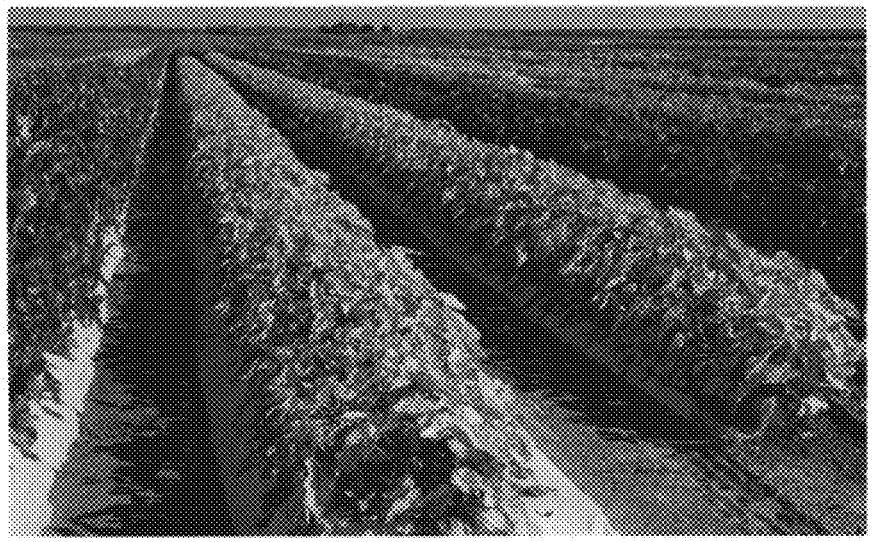
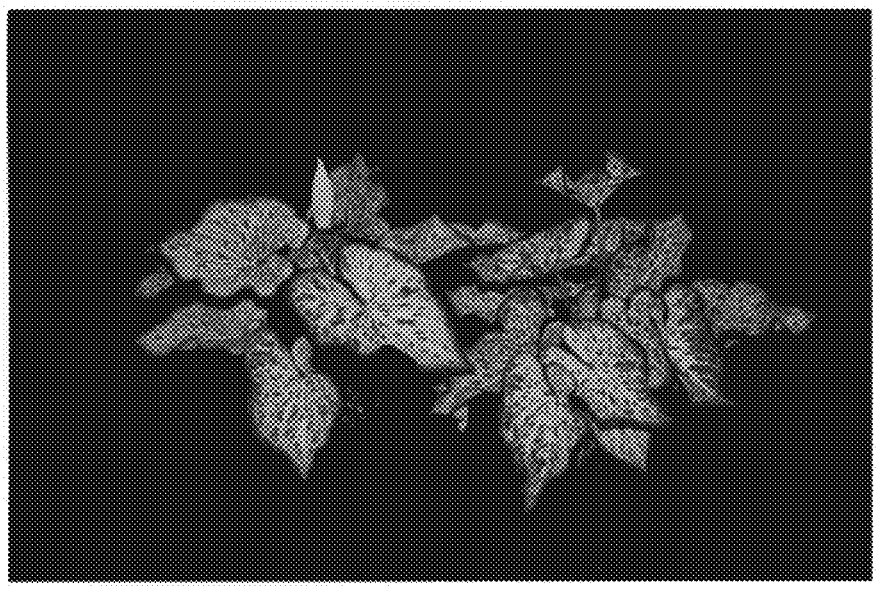

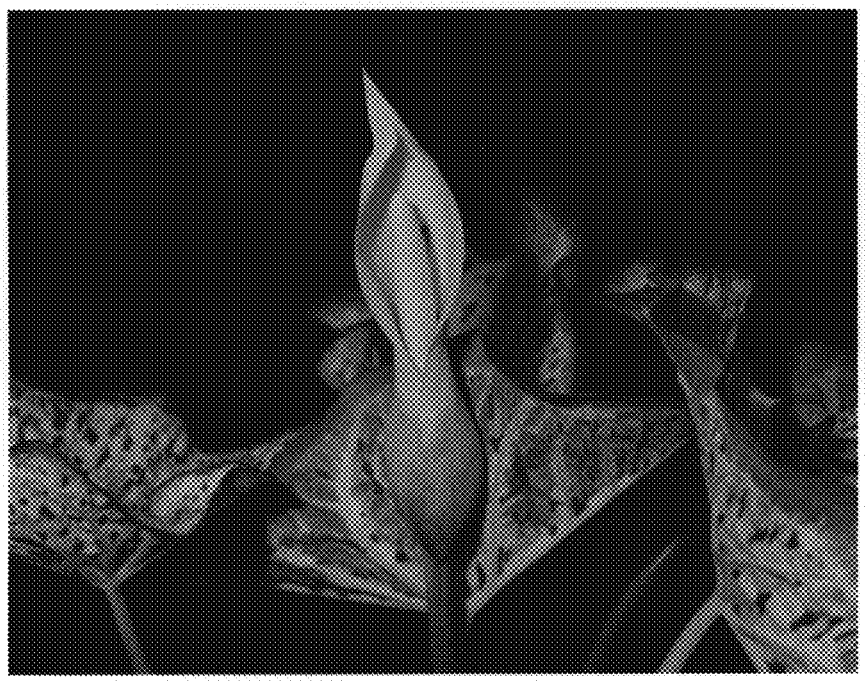
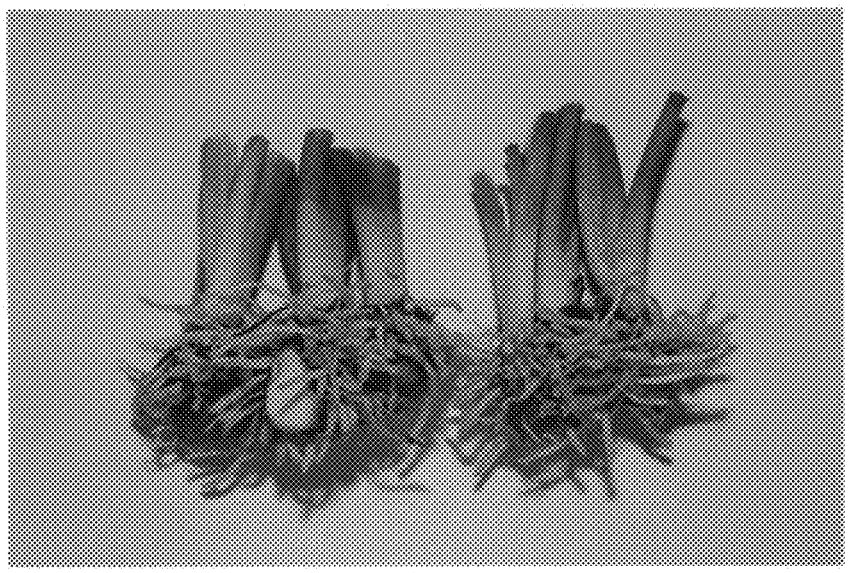

* * * * *